(12) United States Patent
Little, III et al.

(10) Patent No.: US 11,714,037 B2
(45) Date of Patent: *Aug. 1, 2023

(54) SYSTEM AND METHOD FOR DETERMINING VAPOR PRESSURE OF PRODUCED HYDROCARBON STREAMS VIA SPECTROSCOPY

(71) Applicant: JP3 Measurement, LLC, Austin, TX (US)

(72) Inventors: Joseph Paul Little, III, Austin, TX (US); Jie Zhu, Katy, TX (US)

(73) Assignee: JP3 Measurement, LLC, Austin, TX (US)

( * ) Notice: Subject to any disclaimer, the term of this patent is extended or adjusted under 35 U.S.C. 154(b) by 896 days.

This patent is subject to a terminal disclaimer.

(21) Appl. No.: 16/547,387

(22) Filed: Aug. 21, 2019

(65) Prior Publication Data

US 2020/0049604 A1   Feb. 13, 2020

Related U.S. Application Data

(63) Continuation of application No. 14/609,191, filed on Jan. 29, 2015, now Pat. No. 10,393,638.

(60) Provisional application No. 61/933,150, filed on Jan. 29, 2014.

(51) Int. Cl.
| | |
|---|---|
| *G01N 7/14* | (2006.01) |
| *G01N 21/3577* | (2014.01) |
| *G01N 21/359* | (2014.01) |
| *G01N 33/28* | (2006.01) |
| *G01N 33/22* | (2006.01) |

(52) U.S. Cl.
CPC ............. *G01N 7/14* (2013.01); *G01N 21/359* (2013.01); *G01N 21/3577* (2013.01); *G01N 33/22* (2013.01); *G01N 33/2829* (2013.01); *G01N 2201/06113* (2013.01); *G01N 2201/129* (2013.01)

(58) Field of Classification Search
CPC .... G01N 7/14; G01N 21/3577; G01N 21/359; G01N 33/22; G01N 33/2829; G01N 2201/06113; G01N 2201/129
USPC ........................................................ 73/64.45
See application file for complete search history.

(56) References Cited

U.S. PATENT DOCUMENTS

| | | | | |
|---|---|---|---|---|
| 4,153,837 A | * | 5/1979 | Ross | ................... G01N 21/3504 250/343 |
| 4,205,913 A | * | 6/1980 | Ehrfeld | .............. G01N 21/3504 250/343 |

(Continued)

*Primary Examiner* — Marrit Eyassu
(74) *Attorney, Agent, or Firm* — Dubois, Bryant & Campbell, LLP; William D Wiese

(57) ABSTRACT

An NIR analyzer with the optical probes across a pipe, or in a bypass configuration, after a stabilizer in an oil or condensate production plant. Prior to use, liquid samples from the plant are analyzed in a chemical lab to obtain reference vapor pressure or compositional values. A chemometric model using known techniques is then built with the captured absorption spectra and the reference lab results. Preprocessing methodologies can be used to help mitigate interferences of the fluid, instrument drift, and contaminate build up on the lenses in contact with the fluid. The chemometric model is implemented through the NIR analyzer as the calibration curve to predict the vapor pressure or other values of the flowing fluid in real time.

14 Claims, 15 Drawing Sheets

(56) References Cited

U.S. PATENT DOCUMENTS

| | | | | |
|---|---|---|---|---|
| 4,581,942 | A | * | 4/1986 | Ogura .................... A61M 16/08 73/861.04 |
| 4,733,557 | A | * | 3/1988 | Baillie ..................... G01N 7/00 73/64.46 |
| 5,499,531 | A | * | 3/1996 | Henderson ......... G01N 33/2829 73/19.01 |
| 5,717,209 | A | * | 2/1998 | Bigman ............... G01N 21/359 250/339.12 |
| 2009/0153854 | A1 | * | 6/2009 | Taylor-Hayward .......................... G01N 21/359 356/246 |
| 2012/0285896 | A1 | * | 11/2012 | Black ..................... F04B 13/00 210/741 |

\* cited by examiner

| Parameter | Value |
|---|---|
| C1_3 [mol%] | 0.05 |
| C2_3 [mol%] | 7.84 |
| C3H6_3 [mol%] | 0.41 |
| iC4_3 [mol%] | 0.33 |
| nC4_3 [mol%] | 0.00 |
| Normalization Factor | 99.72 |
| C5+_3 | 0.000 |
| T2C5+_3 | 0.348 |
| QC5+_3 | 1.261 |
| Calculated_BTU [per scf] | 2452.17 |
| TVP_3 [psi] | 205.61 |

Scan Date/Time  ID 272592
Pressure [psi] 262.00  Transmission 8.29  Alarm 0
Valve 0
Hourly [bbls]  Previous [bbls]

Wavelength (nm): 1450 1500 1550 1600 1650 1700 1750 1795

FIG. 7

SYSTEM AND METHOD FOR DETERMINING VAPOR PRESSURE OF PRODUCED HYDROCARBON STREAMS VIA SPECTROSCOPY

PRIORITY STATEMENT UNDER 35 U.S.C. § 119

This non-provisional application is a continuation of U.S. patent application Ser. No. 14/609,191 filed Jan. 29, 2015, in the names of Joseph Paul Little, III and Jie Zhu entitled "SYSTEM AND METHOD FOR DETERMINING VAPOR PRESSURE OF PRODUCED HYDROCARBON STREAMS VIA SPECTROSCOPY", which claims priority based upon prior U.S. Provisional Patent Application Ser. No. 61/107,870, filed Jan. 29, 2014, in the name of Joseph Paul Little, III and Jie Zhu, entitled "SYSTEM AND METHOD FOR DETERMINING REID VAPOR PRESSURE," the disclosure of which is incorporated herein by reference.

BACKGROUND OF THE INVENTION

In a fluid processing plants, the plant operating company may or may not own all of raw feed stock. Feeds may come from differing sources, and the operating contracts for product fluids may be different for varying sources. Also, the economics of operation are dependent on inlet compositions, flow rates, current prices on various spot markets, and contractual requirements on products. As a result, plant optimization requires detailed real-time analysis of multiple input and product streams.

From a processing perspective, raw inlet fluid may be from nearby oil or gas fields, be a product of another type of process, or be associated oil or gas from oil field operations. Each has a different composition, and may have different owners. During processing, the facility must be able to account for all compositional changes along the process and how it affects different owners, while also optimizing yields and cash flow.

In addition, some components of the composition may be more desirable than others. For example, condensate has been coming in from gathering systems for years and has been handled in different ways. However, the industry's focus on liquids-rich resource plays has elevated the focus on condensates and how they should be handled. Numerous factors—varying from economical to environmental drivers—have contributed to this change in priorities, but U.S. condensate production has increased in step with activity in shale plays.

Condensate is lighter than crude oil, but heavier than natural gas liquids. The issue with condensate in its natural form is that the lighter hydrocarbons can make it dangerous to store and transport. Therefore, stabilizing is required to allow the condensate to meet specifications. Often, the condensate is pumped to a sales storage tank, where it will flash off its lighter hydrocarbon components, which usually are captured through vapor recovery compression in order to prevent venting to the atmosphere, which results in lost revenues and potential emission issues.

In many cases, however, liquids pricing makes it advantageous to further process the demethanized condensate to produce a saleable condensate product. In this case, the target specification is 9.0 psi Reid vapor pressure (RVP). To accomplish this, a second stabilizer is placed in the process immediately downstream of the first. The demethanized liquids are sent to another liquid/liquid exchanger to be warmed to 110 degrees, and are then fed to the top tray of the RVP control stabilizer.

Measuring the RVP of stabilized condensate in the midstream gathering and stabilization facilities of the more recent shale oil fields has proven to be a very difficult analysis due to the amount of paraffin in the condensate stream. RVP is defined as the absolute vapor pressure of a liquid at 100° F. (37.8° C.). True Vapor Pressure ("TVP") is also of interest, but is much more difficult to determine in the field as it is a partial pressure calculation based on compositional analysis performed to determine the individual components of a complex fluid. From a profitability point of view, oil and gas companies would like to maximize the vapor pressure of their produced liquids while keeping the vapor pressure below any tariff or safety value set for a specific hydrocarbon product or stream. Continuous vapor pressure monitoring is desired in order to optimize the value of production streams while maintaining safe operating parameters.

Before online vapor analyzers were available, samples were extracted from process lines and taken to a lab for analysis. This demanded significant resources and, by definition, could not provide continuous vapor pressure values for a flowing line or a transportation or storage vessel in the field. Additionally, excessive care must be taken using extractive sampling methodologies to ensure that the sample taken to the lab is representative of the process stream. Fluids with high vapor pressures, which are the most critical to monitor, are subject to contamination and vapor loss leading to erroneous results, due to the propensity of the lighter molecules to "flash-off" during the sampling process or in transport to the lab. This can result in a lower vapor pressure reading than was actually present at the time of sample extraction. Therefore, the best methodology to determine vapor pressure of a process fluid would be to perform the measurement in a closed loop system at process conditions.

Conventional online vapor pressure analyzers such as, for example, ABB's RVP4500 series of products, utilize an extractive sampling system, then apply an automatic ASTM D323, ASTM D6377, or similar method to measure the vapor pressure. One of the biggest issues with these online analyzers is paraffin build-up in the system. As the temperature of the product is brought down to the 100° F. required for measurement, the paraffinic material has a tendency to drop out and clog the system, requiring extensive intervention to get back online. Also, it can take considerable time for the conventional online analyzer to complete the analysis. The cycle time is usually more than 10 minutes. Monitoring the outlet of stabilizing unit has shown that the vapor pressure can fluctuate significantly over the course of just a few minutes.

Measuring vapor pressure in the field under real pressure and temperature conditions is nearly impossible to model or calculate based on compositional values. There is no known way to, for example, take a GC's compositional values and use a look-up table or chart to determine RVP. The prior art teaches that the only known way to determine vapor pressure of a fluid is to is to measure the actual vapor pressure (i.e., measuring how much pressure a fluid's out-gassing fumes exert on a containment vessel at a given temperature). Field systems known in the art use some form of this technique to emulate the laboratory techniques to do this.

In contrast, embodiments of the present invention use information from the entire spectra of a fluid to create a chemometric model which correlates that spectra to a measured RVP or TVP value. NIR spectroscopic analyzers have been proven to be able to measure energy content, chemical composition and contaminants in-situ and in real time. Since the chemical composition, especially the ratios of hydrocarbon constituents, determines the fluid properties such as vapor pressure at given temperatures, it is possible to apply the NIR absorption spectroscopy method to predict RVP, TVP and other oil and gas properties.

There is a need, therefore, to monitor the composition of all applicable inlet and product streams and determine the optimum operating conditions for the facility, which may change over time as the economic value of various products change and to measure the RVP of stabilized condensate in the midstream gathering and stabilization facilities of the more recent shale oil fields.

SUMMARY OF THE INVENTION

The present invention provides a system and method to determine Reid vapor pressure ("RVP"), true vapor pressure ("TVP") and other properties of a liquid fluid using near infrared ("NIR") spectroscopy techniques. Swept source lasers or scanning lasers provide sufficient signal and resolution which enables absorption spectroscopy to penetrate through thick fluids, including low API gravity oil. In order to account for source drift and ensure wavelength accuracy, small portions of the signal from the laser cavity may be split off and run through etalon filters. The frequency and amplitude are constantly monitored and fed back to the laser driver modules to maintain consistency from scan to scan.

The chemical composition of a fluid within a fluid infrastructure may be measured using optical sensors that perform spectrographic analysis. These sensors may be placed at various locations within the fluid infrastructure and may be monitored locally or remotely. The remote optical sensors and other sensors may be communicatively coupled to a data gathering location. This allows the sensors to report the chemical composition associated with fluid.

In one embodiment, an NIR analyzer is installed with the optical probes across the pipe or with bypass configuration after a stabilizer of an oil or condensate production plant. Prior to use, liquid samples from the plant are analyzed in a chemical lab to obtain reference vapor pressure or compositional values. A chemometric model using known techniques such as partial least square, classic least squares or principle component regression, is then built with the captured absorption spectra and the reference lab results. The spectra can be subject to preprocessing methodologies, such as first and second or derivatives, extended multiplicative scattering correction, mean centering, and auto scaling, to name a few. The preprocessing methodologies can be used to help mitigate interferences such as cloudiness, or optical transmissibility, of the fluid, instrument drift, and contaminate build up on the lenses in contact with the fluid. The preprocessing methodologies also act as noise filters to enable models to focus on the real compositional changes in the fluid that may affect the resultant vapor pressure of the liquid. After that, the chemometric model is implemented to the NIR analyzer as the calibration curve to predict the vapor pressure or other values of the flowing fluid in real time.

In one embodiment, the vapor pressure value predicted by the NIR analyzer is monitored to control the process of the stabilizer in real time. The light source in the NIR analyzer scans a continuous scan of wavelengths from 1350 nm up to 1800 nm with a very high resolution, 0.5 nm or better. The light passes through the liquid fluid in the optical cell for at least one time before reaching a photodiode. The photo signal is converted to an absorption spectrum that is determined by the chemical composition of the fluid. During the calibration process, random samples are taken while the corresponding spectra are captured.

Because the vapor pressure of a liquid is determined by analyzing the compositional make-up of the fluid stream in real time, concentrations of specific hydrocarbon species can also be determined using the same methodology. For example, the mol % of octane could be reported at the same time as vapor pressure. Additionally, the process could report the presence of contaminates such as basic solids and water content.

The foregoing has outlined rather broadly certain aspects of the present invention in order that the detailed description of the invention that follows may better be understood. Additional features and advantages of the invention will be described hereinafter which form the subject of the claims of the invention. It should be appreciated by those skilled in the art that the conception and specific embodiment disclosed may be readily utilized as a basis for modifying or designing other structures or processes for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein:

FIG. 7 shows the output of a spectroscopic analyzer showing compositional analysis and RVP in real time;

DETAILED DESCRIPTION OF THE INVENTION

Figure 1:
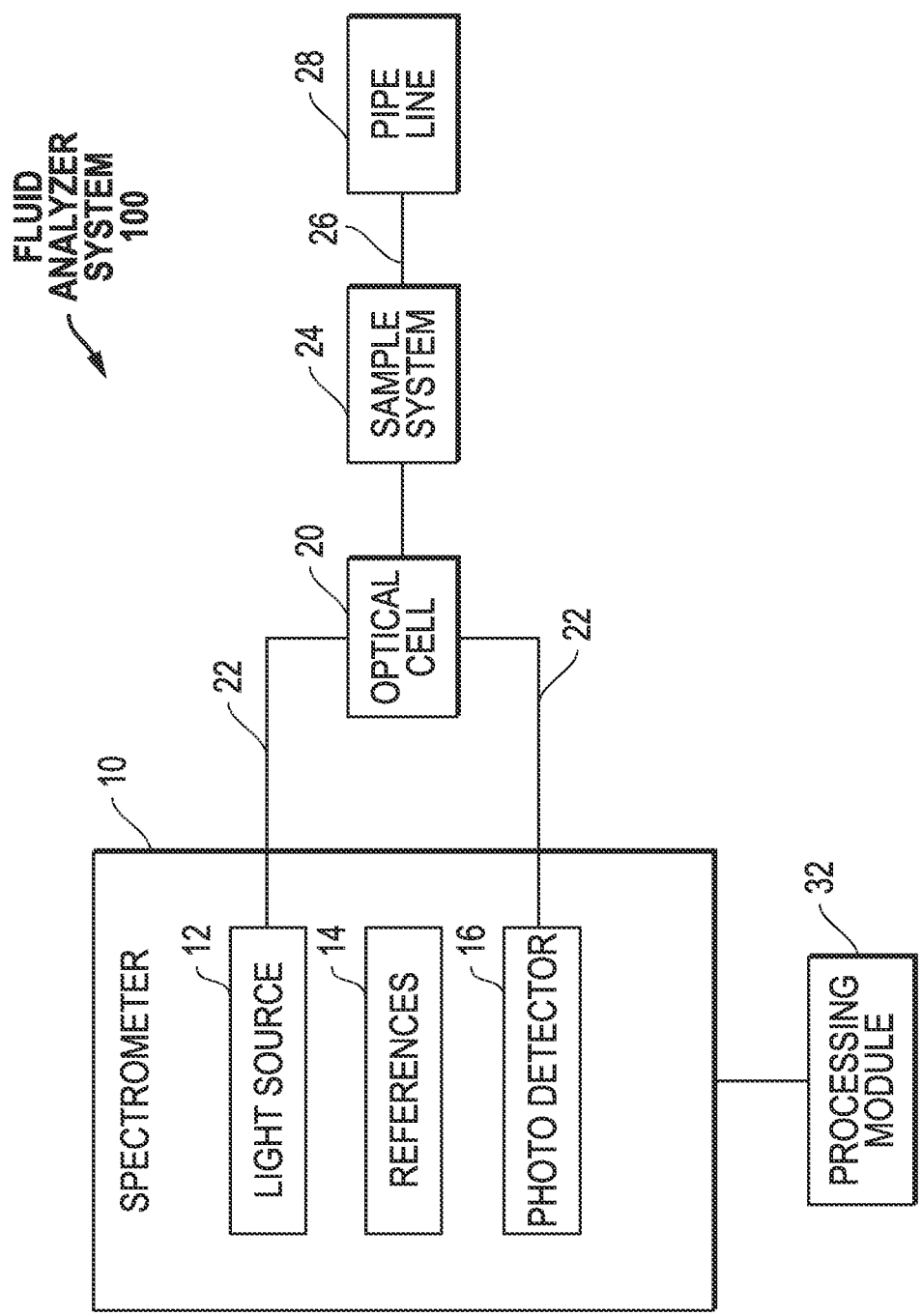
FIG. 1 provides a block diagram of a spectrometer operable to perform spectrographic analysis of fluid in the field.

The present invention is directed to improved methods and systems for, among other things, determining vapor pressure of produced hydrocarbon streams via spectroscopy. The configuration and use of the presently preferred embodiments are discussed in detail below. It should be appreciated, however, that the present invention provides many applicable inventive concepts that can be embodied in a wide variety of contexts other than as described herein. Accordingly, the specific embodiments discussed are merely illustrative of specific ways to make and use the invention, and do not limit the scope of the invention. In addition, the following terms shall have the associated meaning when used herein:

"fluid infrastructure" means any infrastructure used in connection with the collection, processing, storage, transmission or distribution of a fluid including, without limitation, if the fluid is a hydrocarbon, any infrastructure between the wellhead and the point of retail delivery;

"fluid" means any gas or liquid, including but not limited to a natural gas stream with or without suspended liquids, a natural gas liquids (NGL) stream, or a crude oil stream;

means NIR scans with resolution in the 0.5 nanometer to 5 nanometer range;

"NIR" and "near infrared" mean the wavelength range between approximately 1350 to 2500 nanometer, or 1.35 to 2.5 micrometer;

"scanning source" means any light source known in the art for scanning the near infrared spectrum, including tunable diode lasers and broadly scanning lasers; and "TDL" means a tunable diode laser, typically used with very narrow beam width at a single set wavelength corresponding to highest absorption of a molecule of interest in a spectroscopic system.

Embodiments of the present invention utilize NIR spectroscopy to identify the components in condensate in a fluid transmission or storage system that will directly affect the RVP and model the actual RVP of the stabilized condensate. Some embodiments have the ability to report the actual hydrocarbon species along with the RVP information making a significantly more powerful tool for midstream process control.

In some instances, the present invention includes two optical probes that are in contact with the process and may have a heat blanket on them to prevent them from being the cool stop or heat sink for the paraffin that is typically in these condensate streams. The optical probes can be mounted directly off of the stabilizer outlet while the process is still at the higher temperatures which will keep the paraffin in a liquid phase.

Embodiments of the present invention may be used to collect compositional sample points on all of the gas and liquid phase streams. The device may be designed for field use in hazardous areas. It can support up to ten fiber optic trains which may be run out to various sample points in the facility. Each fiber terminates at a field located sample cell, where the sample of gas or liquid is allowed to flow between two optical windows through which the infrared beam of light passes. The sample points are typically operated at line temperatures and pressures. Real time data analysis and results allow for optimization of the plant performance, calculating material balances, and facilitate debottlenecking operations and maximizing plant physical and economic performance by improving the control of towers, separators, and stabilizers.

As previously discussed, embodiments of the present disclosure provide a way of optically determining the chemical composition of a fluid such as but not limited to natural gas, to derive the RVP and other like properties associated with the fluid. Embodiments may employ the near infrared (NIR) band of the electromagnetic spectrum, specifically between the 1300 nm to 2500 nm range. One embodiment focuses on the 1550 nm to 1800 nm range for the carbon hydrogen overtone to resolve the chemicals that contribute energy content to the fluid.

Another embodiment of the present disclosure provides a way of electronically gathering and reporting optically determined chemical compositions of a fluid. The disclosure describes an in-line process of gathering, transmitting, and storing data obtained using the NIR band of the electromagnetic spectrum, specifically between the 1300 nm to 2500 nm range. The information may be used to make various decisions affecting the stabilizer in a production plant based on the real-time feed or historically trended data from the instruments.

NIR spectrographic analysis provides a non-invasive optical measurement that has no emissions. Unlike GCs, occasional liquid condensate introduction will not destroy expensive components in an NIR spectrometer. Therefore, NIR spectrographic analysis allows a more environmentally friendly and significantly cheaper cost of ownership than conventional chromatography.

An exemplary spectrometer 10 shown in FIG. 1 may be used by embodiments of the present disclosure.

Spectrometer 10 includes a light source 12, integrated wavelength and amplitude references 14, and a photo detector 16. The light source 12 may be a laser, such as but not limited to a tunable diode laser or tunable super light emitting diode laser, that may be used to scan the spectrum or portions of the spectrum to be sampled. Spectrometer 10 may be coupled to an optical cell 20 via fiber optic cables 22. A sample system 24 extracts fluid 26 from the pipe line 28, measure the pressure and temperature of the fluid, direct the fluid through optical cell 20 where it will be exposed to light from the light source 12, and reintroduce the sample in the transmission line 28 or exhaust it. The sample system may need to be heated in certain installations in order to keep the fluid above the dew point temperature. The spectral data may be transmitted back to the photo detector 16 via the fiber optic cables 22. In one embodiment the detector array may be an Indium Gallium Arsenide (InGaAs) photo detector. Electronics (processing module 32) processes the spectrographic image to determine the image's energy content and chemical composition. Other properties of the fluid, such RVP, can also be computed from the compositional information. The results will then be stored for a later transmission and analysis or sent directly to a data gathering location.

The processing module 32 may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions. The memory may be a single memory device or a plurality of memory devices. Such a memory device may be a read-only memory, random access memory, volatile memory, non-volatile memory, static memory, dynamic memory, flash memory, cache memory, and/or any device that stores digital information. Note that when the processing module 32 implements one or more of its functions via a state machine, analog circuitry, digital circuitry, and/or logic circuitry, the memory storing the corresponding operational instructions may be embedded within, or external to, the circuitry comprising the state machine, analog circuitry, digital circuitry, and/or logic circuitry.

Embodiments of the present disclosure may employ chemometric models and other analytical techniques to determine the composition of the fluid 26. The data models are used to compare the spectrums gathered by spectrometer 10 from the fluid 26 flowing through the sample cell 20 with known results. The models will be built from a variety of different sources. Parts of the models are created by correlating output values from a GC with the spectrum of the same fluid. In addition to the GC correlation, one may mix fluids of known composition and record their respective spectrums using the spectrograph. Pressure and temperature may be recorded to account for their effects. Any offsets or adjustments required will be included in the calibration models. All of this information is compiled and used as a reference to compare the information coming from the online monitor. The calibration set will allow one to derive the sample's RVP and other like information.

Embodiments of the present disclosure have the ability to transmit the data back to a gathering location to keep a recorded history of values. The transmission can be wireless or via hard wire. Some configurations may perform data processing on-board while others will send raw data that will be processed by another computer that has the chemometric models and analytical software.

Power may be provided by a rechargeable battery source that can be replenished by solar power, generator, or hard line electricity. The direct current of the battery source may run through an inverter to achieve alternating current of a 120 or 240 volts at 60 hertz. Alternatively, another embodiment may employ DC to directly power all components and modules. This may be used to power the spectrometer, light source 12, the on-board computing module, pressure transducers, temperature sensing modules, any heating elements, data transmitting equipment, and the valve control manifold for the sampling system. This reduces the required infrastructure needed to support the sensors in the field.

Figure 2:
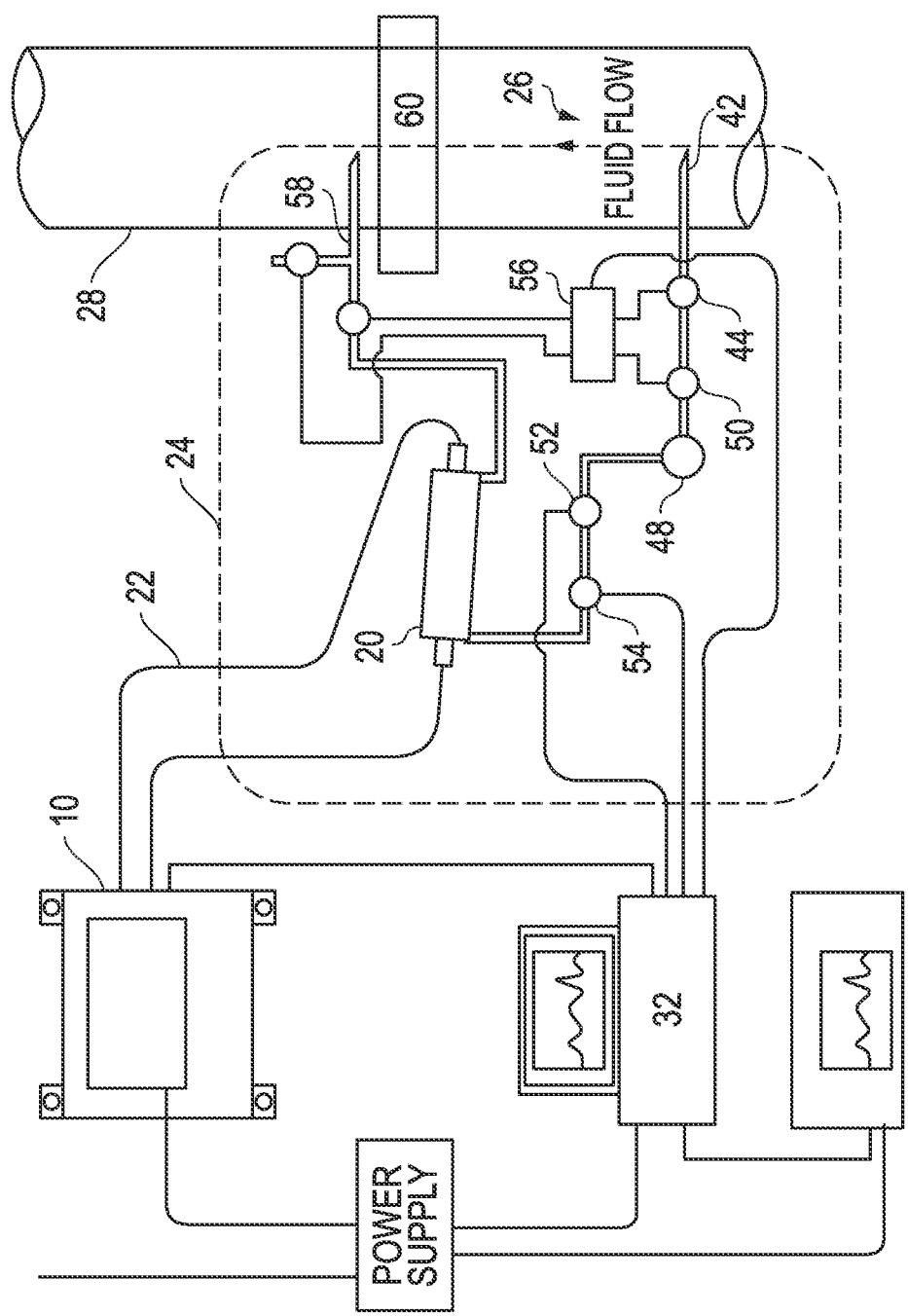
FIG. 2 provides a sample system used in combination with the spectrometer of FIG. 1 in accordance with an embodiment of the present disclosure.

One embodiment of sampling system 24 is shown in FIG. 2. It includes sample probe 42 to extract fluid 26 from the transmission line 28, a shut off valve 44, a switching valve, a filter 48, a flow controller or regulator 50, a pressure transducer 52, a temperature probe 54, an optical cell 20 coupled with fiber optic cables 22, a heater operable to heat the sampled fluid, another flow controller or regulator 56, and a connection 58 to reintroduce the sample fluid or dispose of the sampled fluid. The sample system will preferably operate across a constriction point 60 in transmission line 28 in order to create a pressure differential to flow fluid though the sample loop. Due to the fact that optical measurement is non-invasive, the sample may be reintroduced into the transmission line 28 but may be disposed of if the site set-up is not conducive to reintroduction. A small pump may be used for reintroduction if no pressure delta can readily be established. Sample loop valves may be actuated by a switching manifold controlled by the on-board electronics. The pressure and temperature sensors provide data signals to the on-board electronics to be included in the data log for each respective spectral recording. The signals may, for example, be 4-20 ma analog signals or 0-5 volt DC signals. Pressure through the sampling system may be about 100 psi, although other pressures both higher and lower are contemplated. These spectrographs may be repeated on the order of every 20 milliseconds or as specified by data management requirements. In some embodiments but not all, the spectrometer and electronics may be housed in an enclosure that is explosion proof and rated for Div. 1 Class 1 environments.

Figure 3:
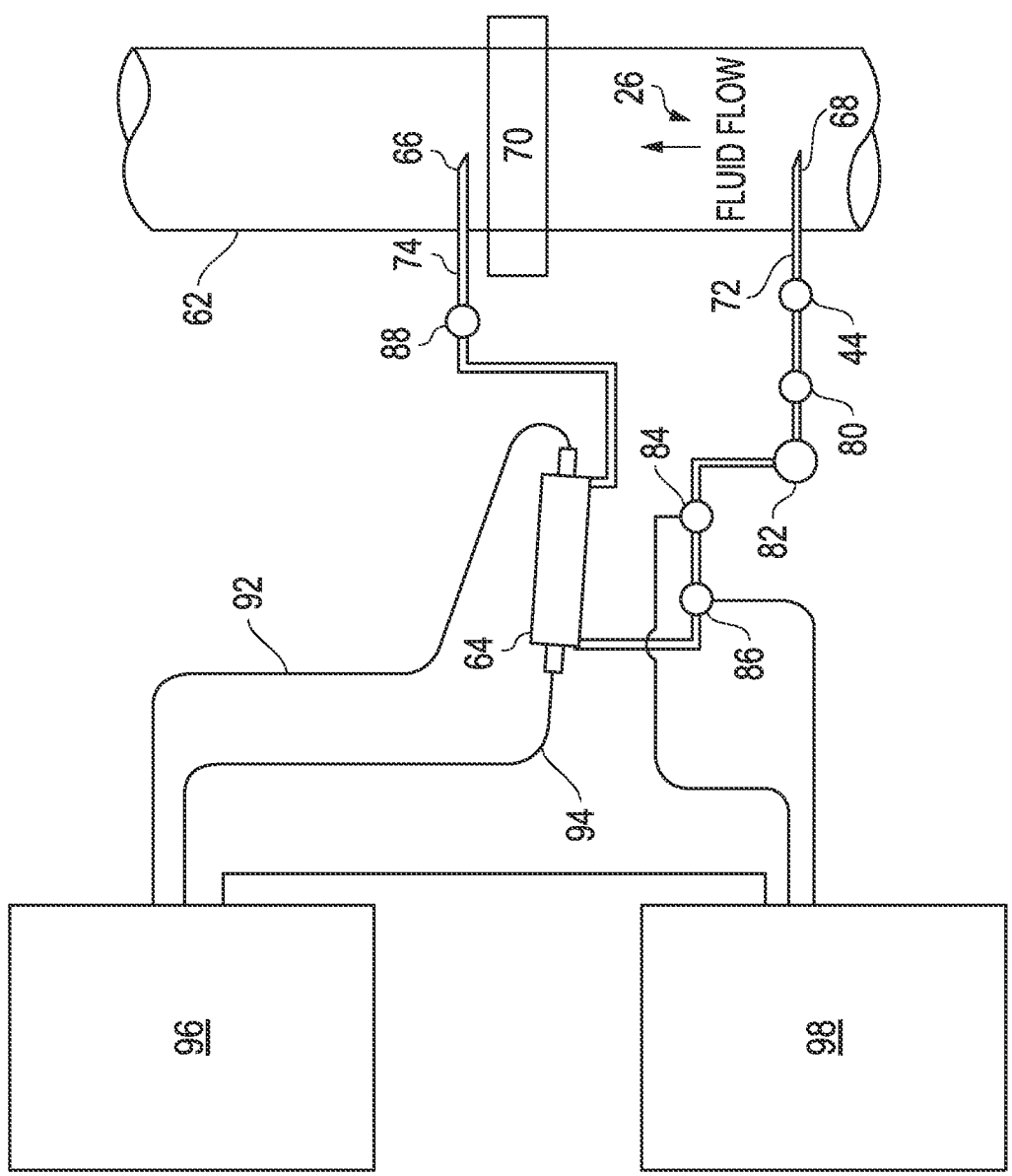
FIG. 3 depicts a another embodiment in accordance with the present disclosure wherein a remote optical sensor is coupled to a fluid infrastructure in accordance with an embodiment of the present disclosure.

FIG. 3 shows another embodiment of the present disclosure wherein a remote optical sensor is used to couple to a fluid infrastructure system. Here fluid flow 26 within a piping infrastructure 62 has a series of physical and chemical properties associated with the fluid. As shown here, optical cell 64 is placed between a low pressure tap 66 and high pressure tap 68 through which sample fluid flows. Differential pressure drives flow through optical cell 64. The embodiments of FIG. 2 and FIG. 3 show how optical cell 64 may be placed in sample lines which may have been previously used to take fluid samples which would have been processed using gas chromatography. High pressure sample line 72 and low pressure sample line 74 may be isolated from the fluid flow 26 using shutoff valves. A flow pressure controller 80 is used to control the amount of flow to optical cell 64. Additionally fluid flow may be filtered using a filter 82. Fluid flow through optical cell 64 is returned through the low pressure line 66 which may further include a low pressure controller 88 wherein flow pressure controller 80 and 88 may be controlled using a control manifold.

Fiber optic cables 92 and 94 may be used to couple optical cell 64 to spectrometer 96. As described previously, this spectrometer may be a NIR spectrometer in order to more efficiently deliver light to and from optical cell 64. A computer or processing module 98 may be used to take the outputs from the spectrometer 96 and other sensors such as temperature sensor 86 and pressure sensor 84 in order to determine the energy content associated with the fluid flow 26.

Figure 4:
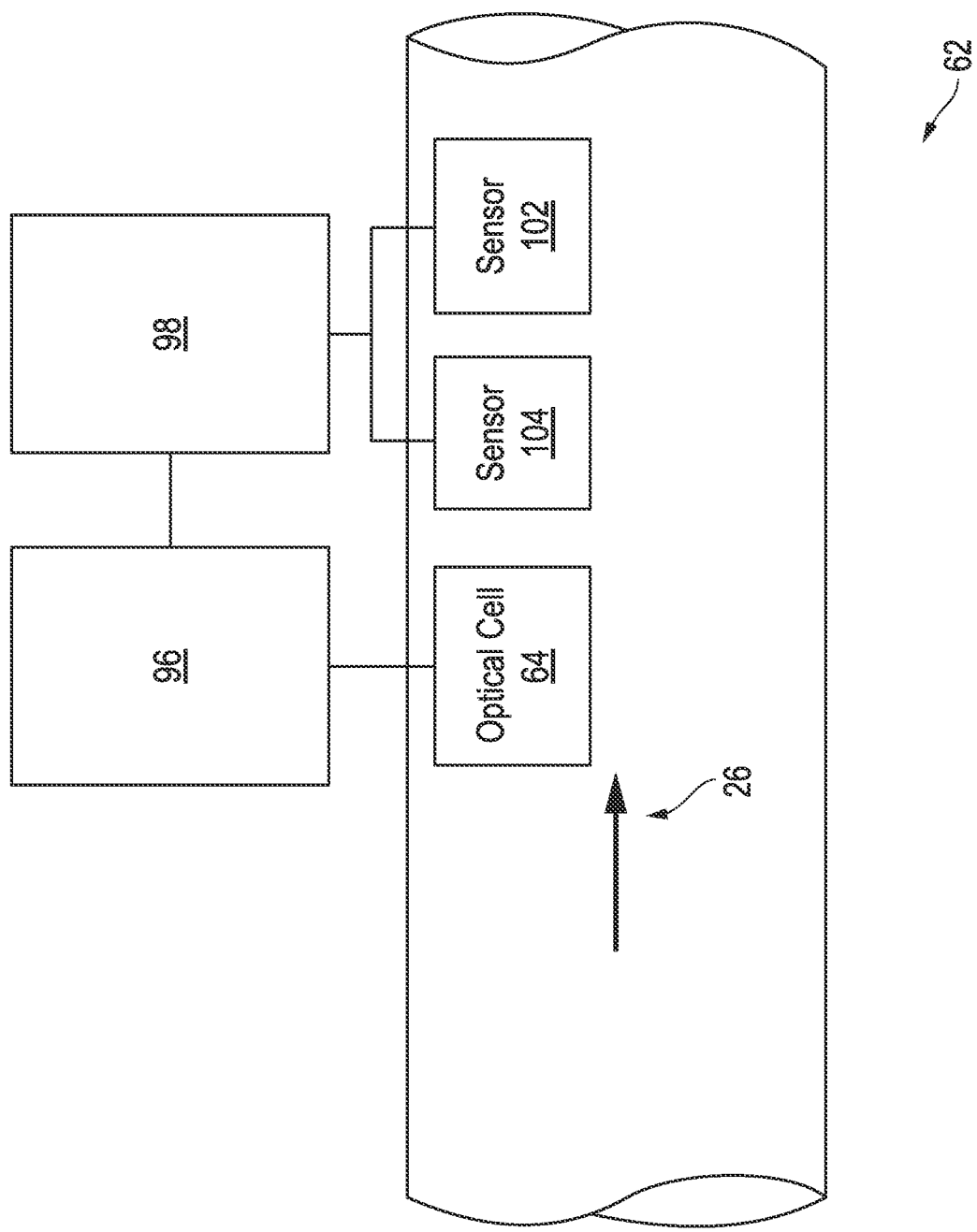
FIG. 4 depicts another embodiment of the present disclosure wherein the optical cell is located within the fluid flow in accordance with an embodiment of the present disclosure in order to eliminate many of the complexities associated with an external sample system.

FIG. 4 depicts a second embodiment wherein the optical cell 64 is located within fluid flow 26. This eliminates much of the need for low pressure lines and high pressure lines. In addition to optical cell 64, other sensors such as pressure sensor 102 and temperature sensor 104 may be located within fluid flow 26 as well. As shown previously, the optical cell may be optically coupled using fiber optics or other like materials to spectrometer 96. Sensors 102, 104 as well as spectrometer 96 may all be communicatively coupled to a processing module 98 which may then determine the chemical composition associated with fluid flow. These individual modules may be coupled wirelessly or via wired connections.

Figure 5:
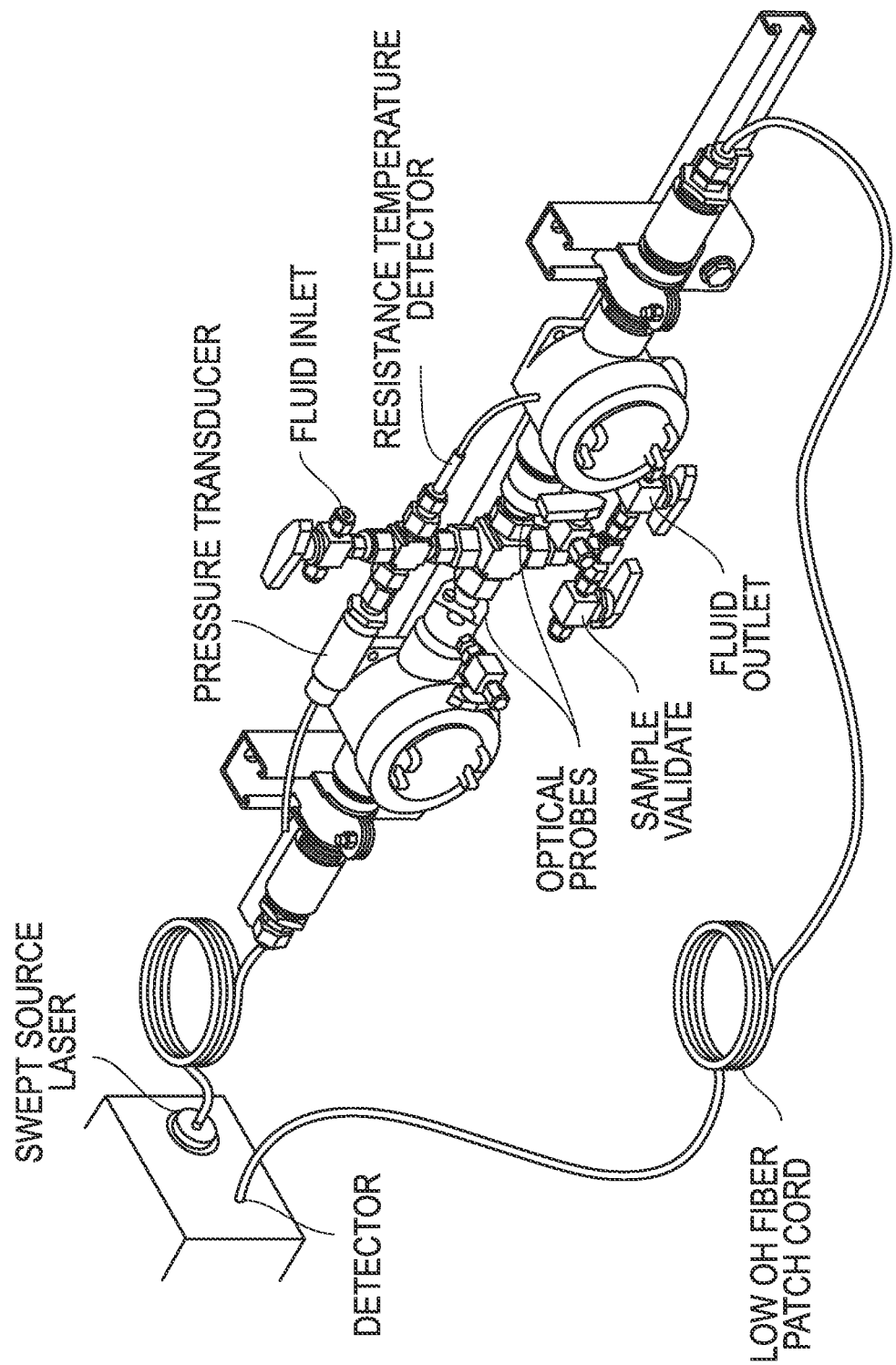
FIG. 5 illustrates a bypass configuration where part of the process stream, at operating temperature and pressure, is diverted through the optical cell.
Figure 6:
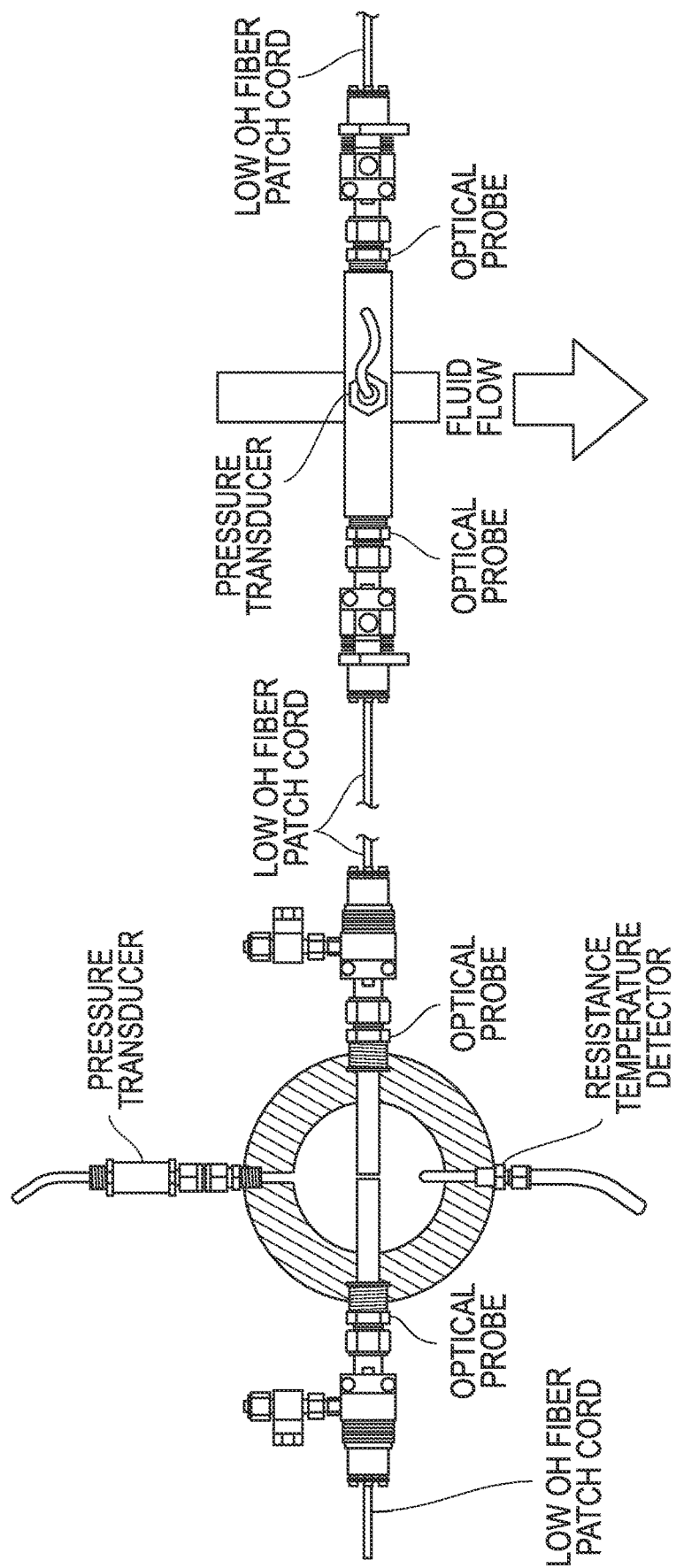
FIG. 6 illustrates a configuration whereas the probes are inserted directly into the main flow line.

FIG. 5 illustrates a bypass configuration where part of the process stream, at operating temperature and pressure, is diverted through the optical cell. FIG. 6 illustrates a configuration whereas the probes are inserted directly into the main flow line. FIG. 7 shows the output of a spectroscopic analyzer showing compositional analysis and RVP in real time.

Spectrographs use chemometric models and other analytical techniques to determine the composition of the fluid. The data models are used to compare the spectrums being gathered by the spectrometer from the fluid flowing through the sample cell with known results. Pressure and temperature will be recorded to account for their effects. Any offsets or adjustments required will be included in the calibration models. All of this information is compiled and used as a reference to compare the information coming from the on-line monitor. The calibration set allows one to derive the sample's RVP. The models may reside on each individual installation or on a central server. The units with all the analytical capabilities on-board will send compiled data while other units may transmit raw telemetry that will be analyzed by a central server. The server will have the chemometric models and other analytical software necessary to complete the analysis.

Figure 8:
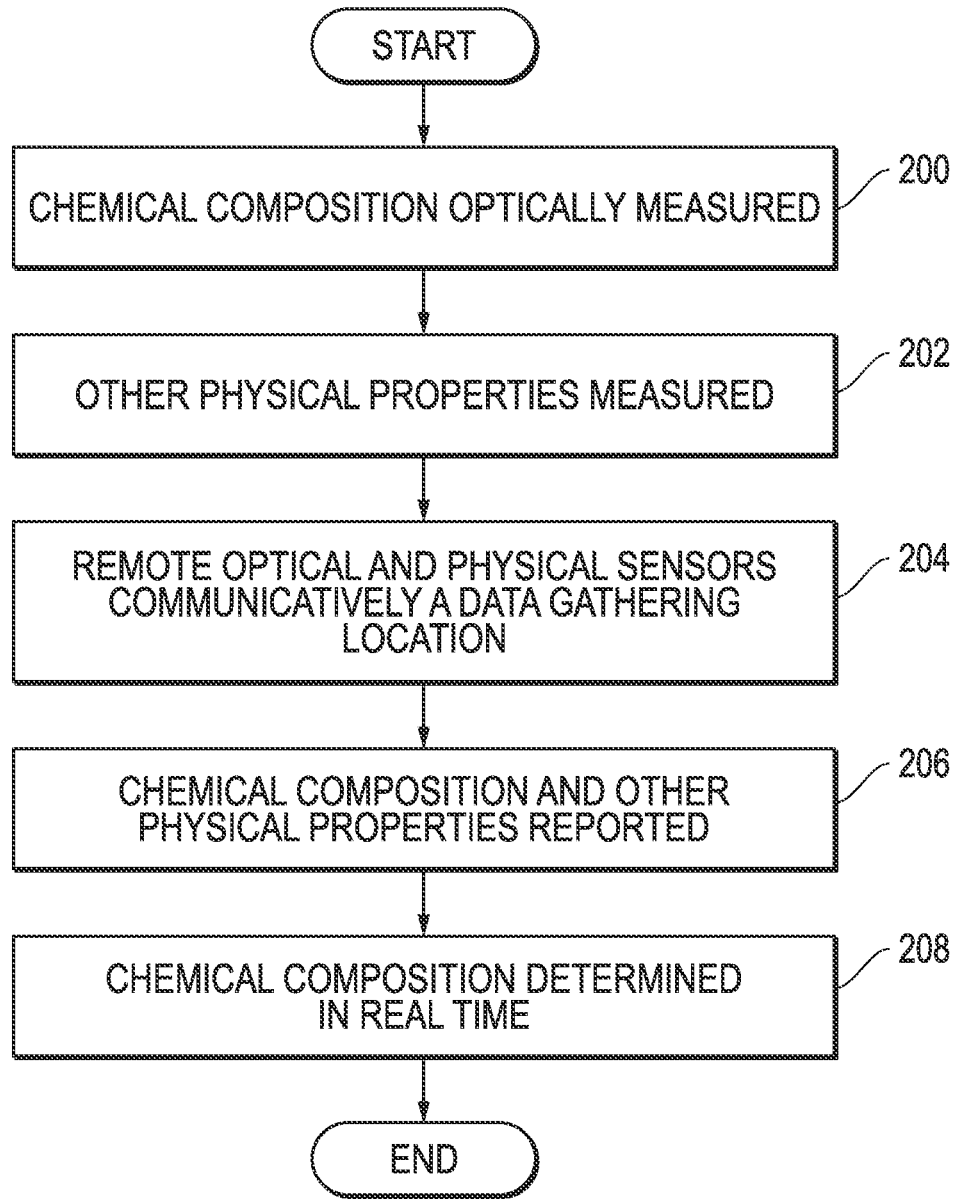
FIG. 8 provides a logic flow diagram in accordance with an embodiment of the present disclosure that describes how the chemical properties of a fluid may be determined using remote optical sensors.

FIG. 8 provides logic flow diagram and a method to optically determine the chemical composition of the fluid in accordance with embodiments in the present disclosure. In Step 200 the chemical composition of the fluid may be optically measured using remote optical sensors within a fluid infrastructure. In Step 202 other physical properties associated with the fluid may be measured. These properties may include temperature and pressure but are not so limited. The chemical composition may be based on the spectrographic analysis performed using remote optical sensors. This information is combined with information such as pressure and temperature to determine overall energy content associated with the fluid. The remote optical and physical sensors may be communicatively coupled in Step 204 to a data gathering location. In Step 206 the chemical composition of the fluid as well as the other physical properties may be reported to a computer processor which may be located locally or at the data gathering location. In Step 208 the chemical composition associated with bulk quantities of the fluid may then be determined in real time. For example, using spectrographic analysis it may be possible to perform samples as often as every 20 milliseconds. This differs greatly from current practices wherein samples are taken perhaps on a monthly or quarterly basis. This analysis allows the downstream user to access this information in order to reconfigure manufacturing processes based on real time chemical compositions of the fluid to be delivered. Direct integration of the measurement systems with the control systems of a processing unit, allows the processing unit to manage valves or other control mechanisms to place various supplies or processes on line or off line. Further, processes can be varied or optimized to ensure control of the chemical processes based on real time chemical measurements.

Yet another embodiment allows this methodology to be applied in the field or gathering location wherein scrubbing and filtering equipment may be placed on or off service based on the quality and contaminants contained within the fluid being supplied to and delivered from the gathering location.

Figure 9A:
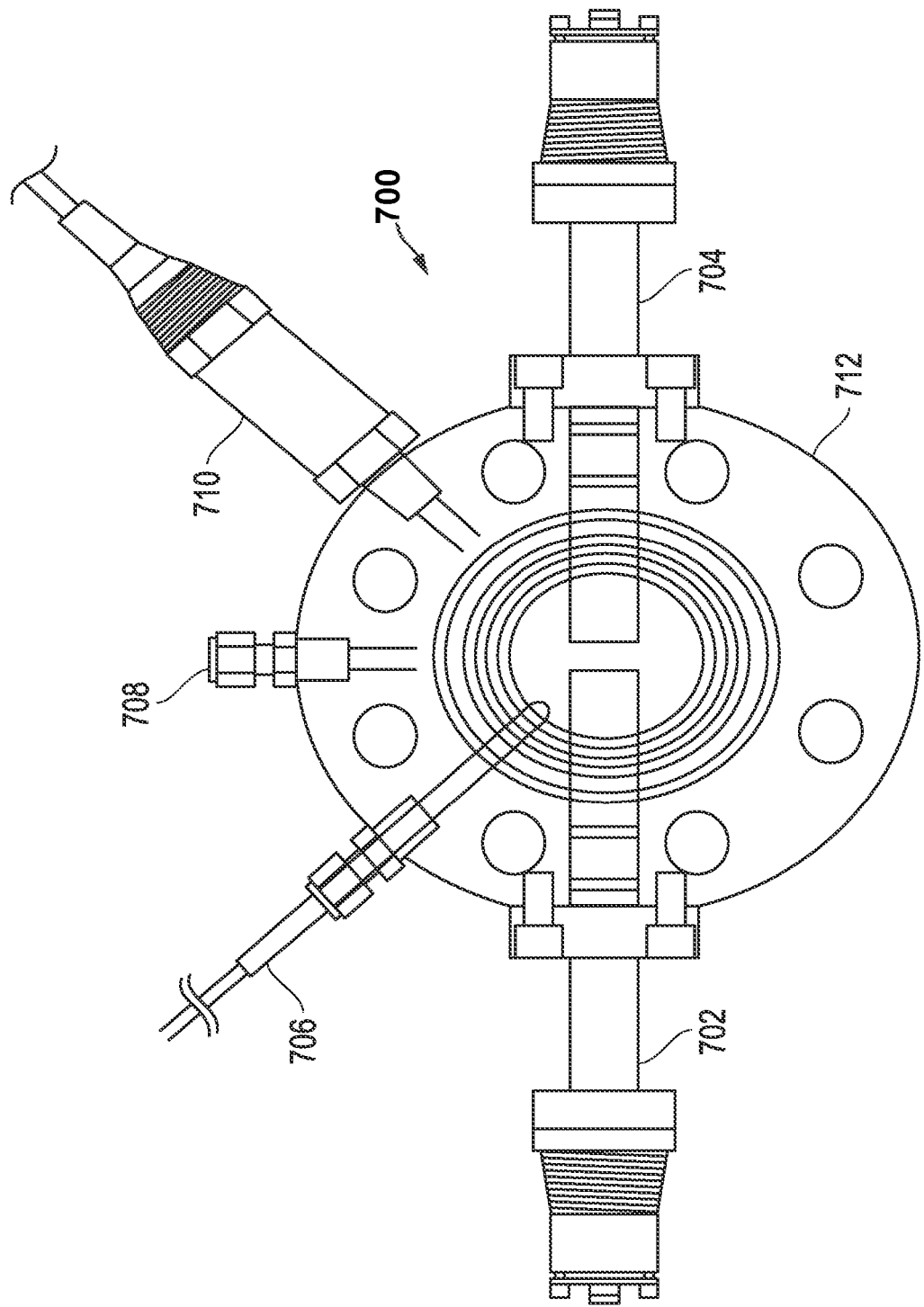
FIGS. 9A-9D picture embodiments of the present disclosure operable to measure the chemical composition of a fluid within a pipeline.

FIG. 9A pictures one embodiment of the present disclosure wherein a flange type device 700 is provided to measure the chemical composition of a fluid within a pipeline. As shown here, chemical composition analyzer 700 includes optical probes 702 and 704, temperature probe 706, a sample port 708, and a pressure transducer. These probes and ports are incorporated within an ANSI compatible flange 712. The optical probes allow spectroscopic measurements to be taken and combined with the results of the pressure transducer 710 and temperature transducer 706 in order to yield information about the quality and quantity of fluids within the transmission pipe in which flange chemical composition analyzer 700 is installed.

Figure 9B:
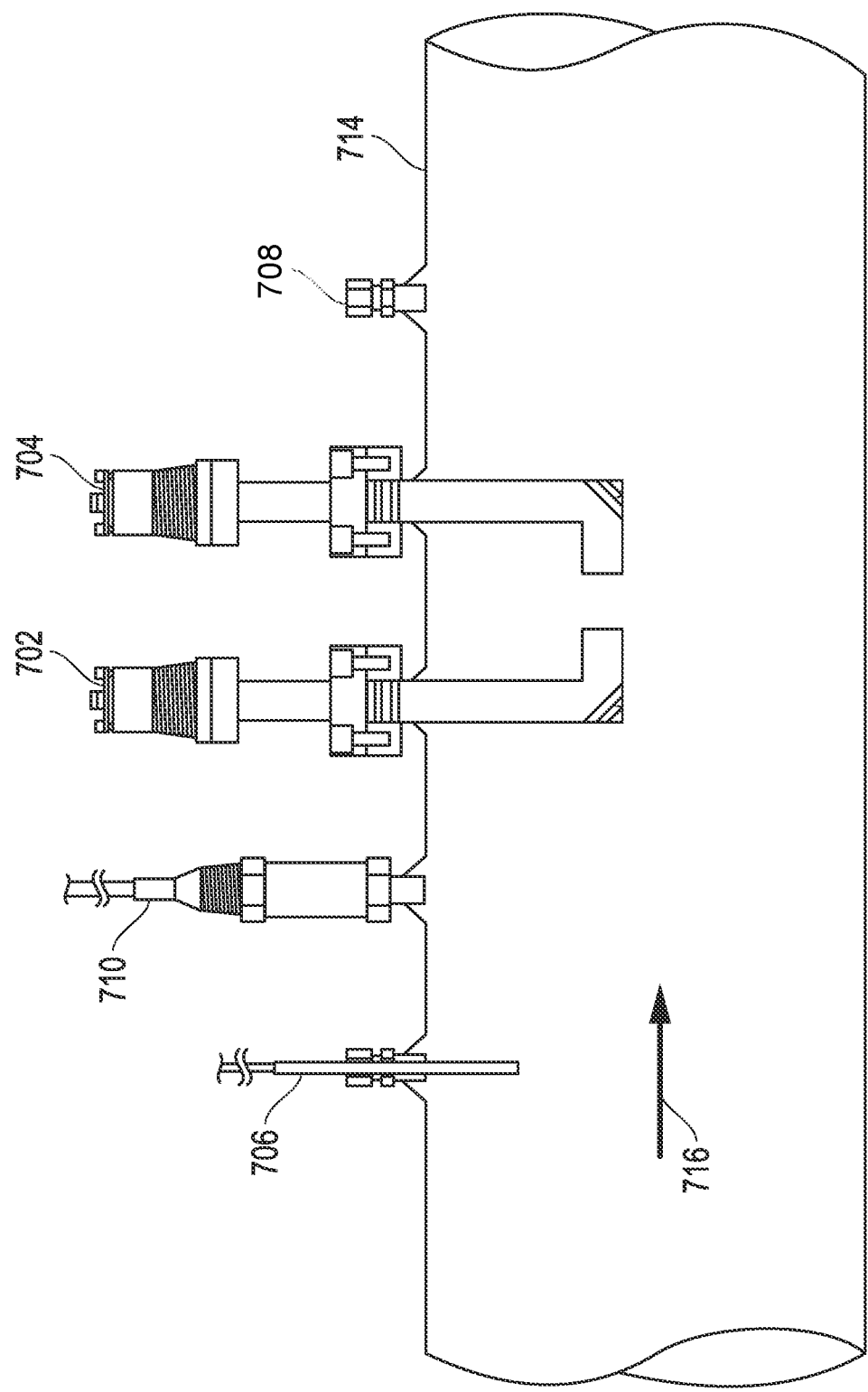

FIG. 9B pictures one embodiment of the present disclosure wherein individual probes are introduced to a large diameter pipe 714 to measure the chemical composition of a fluid within a pipeline. As shown here chemical composition analyzer 700 includes optical probes 702 and 704, temperature probe 706, a sample port 708, and a pressure transducer 710.

These probes and ports are incorporated within an ANSI large diameter pipe 714. The optical probes allow spectroscopic measurements to be taken and combined with the results of the pressure transducer 710 and temperature transducer 706 in order to yield information about the quality and quantity of hydrocarbon fluids within the transmission pipe in which composition analyzer 700 is installed.

Figure 9C:
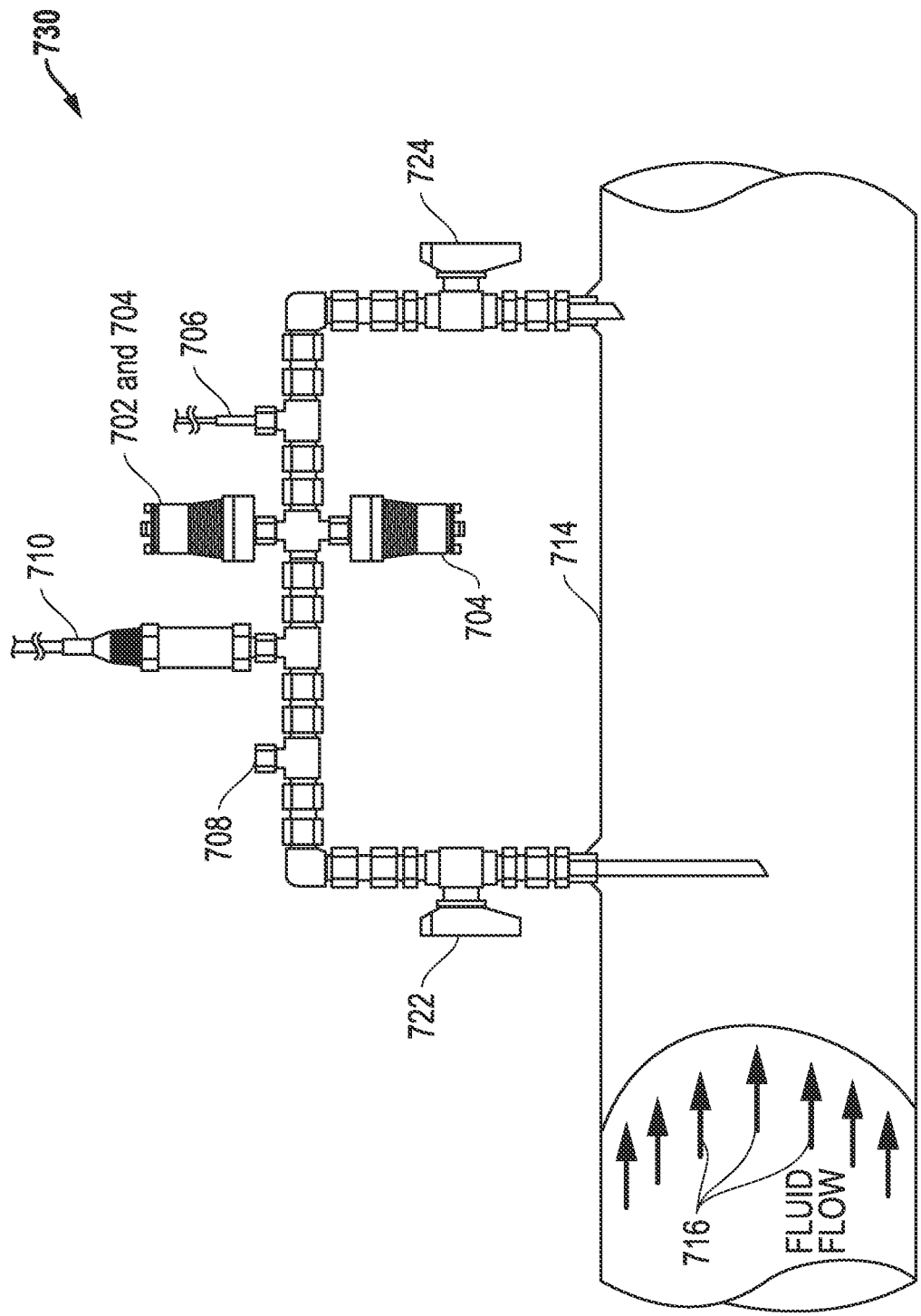

FIG. 9C pictures one embodiment of the present disclosure wherein individual probes are introduced to a large diameter pipe 714 to measure the chemical composition of a fluid within a pipeline using a bypass loop 730. As shown here chemical composition analyzer 700 comprises a bypass loop 730 that includes isolation valves 722 and 724, optical probes 702 and 704, temperature probe 706, a sample port 708, and a pressure transducer 710. The optical probes allow spectroscopic measurements to be taken and combined with the results of the pressure transducer 710 and temperature transducer 706 in order to yield information about the quality and quantity of hydrocarbon fluids within the transmission pipe in which composition analyzer 700 is installed.

Figure 9D:
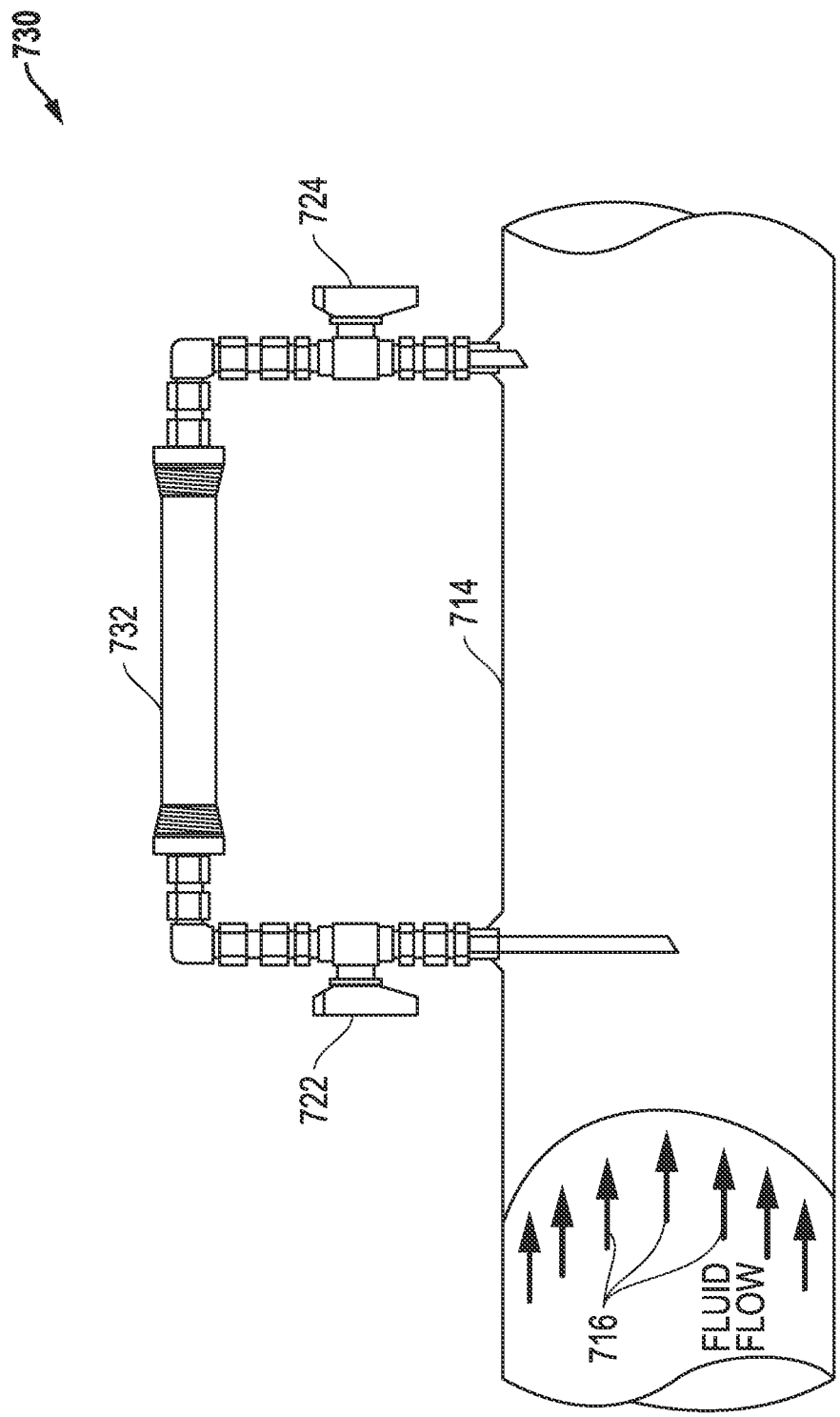

The chemical composition analyzer 700 may be powered from a power generating device operable to extract energy from the fluid flow 716. This may be extracted from the kinetic energy of the fluid flow or directly from the fluid itself. FIG. 9D provides one example where power generating module 732 (e.g. a turbine) is used to extract energy from the fluid flow. This may be in a bypass line 730 or within the pipe 714 itself. A squirrel cage type stator and armature may be used to eliminate the need for electrical penetrations of the pipe.

In certain embodiments, the process of the present invention involves normalizing the 1st derivative spectrum for conditions such as pressure and temperature. In one embodiment, normalizing may be achieved by dividing the 1st derivative spectrum by the pressure (in PSI) and accounting for, mathematically, the effects of temperature for normalization. Temperature normalization may take different forms such as eigenvector values in the calibration matrix or other known means to those having skill in the art. In other embodiments the process may be more complex. One or more calibration models are then applied to the normalized 1st derivative spectrum to calculate items of interest such as RVP. For example, if the spectral abnormality diagnostics are favorable, transmit the results to the appropriate location but, if they are not favorable, prevent any predicted results from being used for control (or other) purposes.

Figure 10:
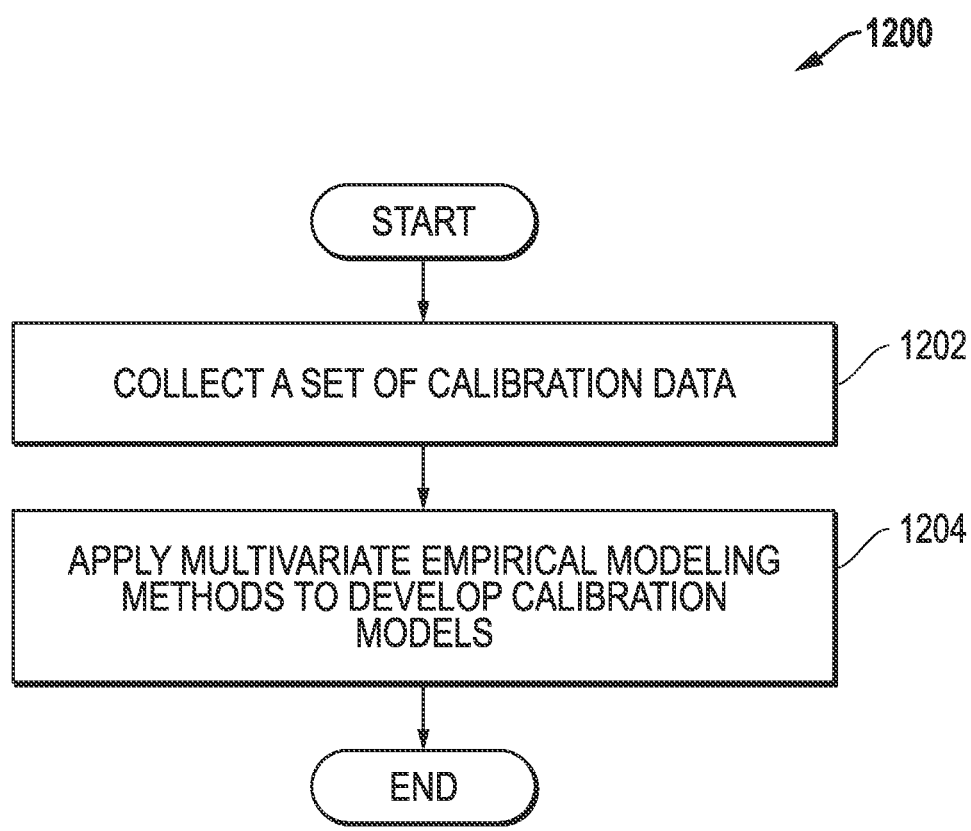
FIG. 10 provides a logic flow diagram describing how the calibration models are developed in accordance with embodiments of the present disclosure.

FIG. 10 provides a logic flow diagram describing how the calibration models are developed in accordance with embodiments of the present disclosure. Calibration development process 1200 begins with step 1202. Step 1202 collects a set of calibration data, to be used to develop the model. This calibration dataset must have matching NIR spectral data (X) and property data (Y). Such data can be collected in several ways, including: (1) injecting fluid samples of known properties into the sample cell, and recording their spectrum as described above; and (2) recording the spectrum of an on-line flowing fluid sample, accompanied by subsequent capture and laboratory analysis of an extracted fluid sample (where the sample was collected at the same time and same location where the spectrum was collected). Step 1204 applies multivariate empirical modeling methods to develop calibration models, given the calibration data collected in 1202. This model development work can involve one or more of the following elements: (1)

Use of principal components analysis (PCA) and partial least squares (PLS) regression to "explore" the calibration data, to uncover optimal modeling strategies and to detect potential outliers in the calibration data set; (2) If any outliers (samples or spectral variables) are detected in the calibration data, exclude them from being used to build the models; (3) Use of partial least squares (PLS) regression, to construct predictive calibration models from the calibration data; this method generates a series of regression coefficients (b) which, when multiplied with the absorbance values (A) of an unknown fluid sample's spectrum, will yield the property of interest; (4) Use of generic algorithms (GA) to select subsets of the spectral response variables to use in the predictive models this is done to make the PLS models more robust with respect to known interfering effects in the spectra; (5) use of PCA to generate an "outlier model", which can be run on-line to assess whether a field-collected spectrum is abnormal, with respect to the spectra that were used to develop the models; this model can be used to generate "spectral abnormality" diagnostics, which can be used as described above.

In one embodiment, an NIR analyzer is installed with the optical probes across the pipe or with bypass configuration after a stabilizer of an oil or condensate production plant. Prior to use, liquid samples from the plant are analyzed in a chemical lab to obtain reference vapor pressure or compositional values. A chemometric model using known techniques such as partial least square, classic least squares or principle component regression, is then built with the captured absorption spectra and the reference lab results. The spectra can be subject to preprocessing methodologies, such as first and second or derivatives, extended multiplicative scattering correction, mean centering, and auto scaling, to name a few. The preprocessing methodologies can be used to help mitigate interferences such as cloudiness, or optical transmissibility, of the fluid, instrument drift, and contaminate build up on the lenses in contact with the fluid. The preprocessing methodologies also act as noise filters to enable models to focus on the real compositional changes in the fluid that may affect the resultant vapor pressure of the liquid. After that, the chemometric model is implemented to the NIR analyzer as the calibration curve to predict the vapor pressure or other values of the flowing fluid in real time.

Figure 11:
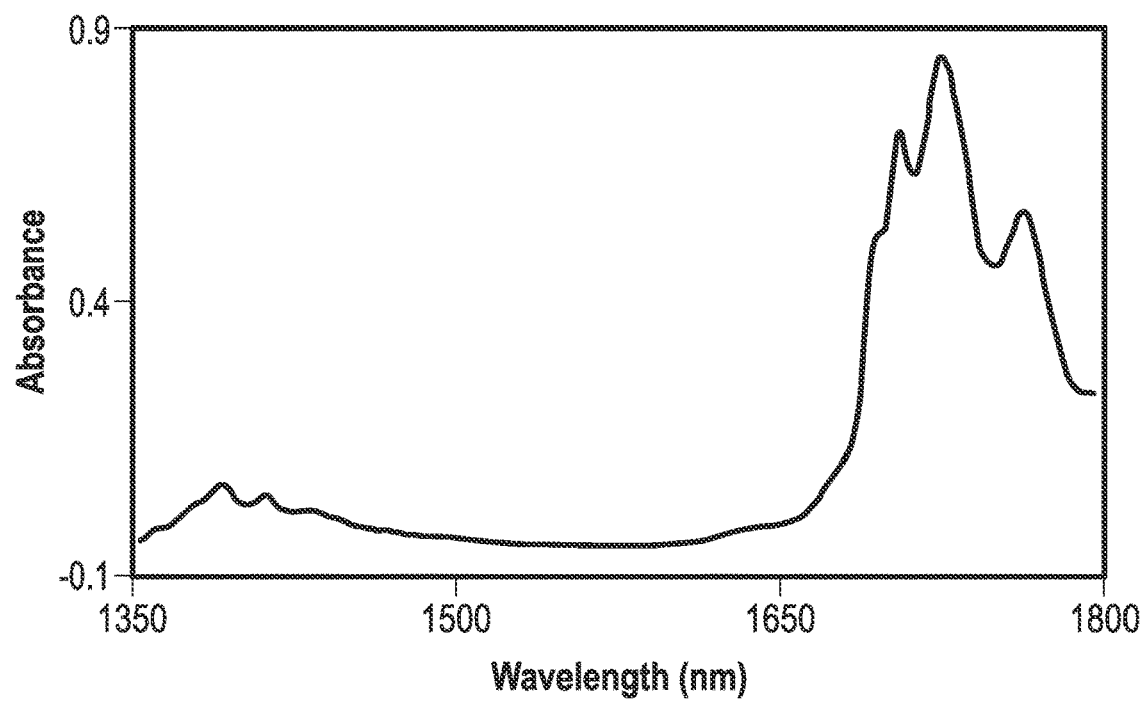
FIG. 11 shows an NIR absorption spectrum of mid-stream production oil after a stabilizer, with the hydrocarbon absorption region is between 1600 nm and 1800 nm.
Figure 12:
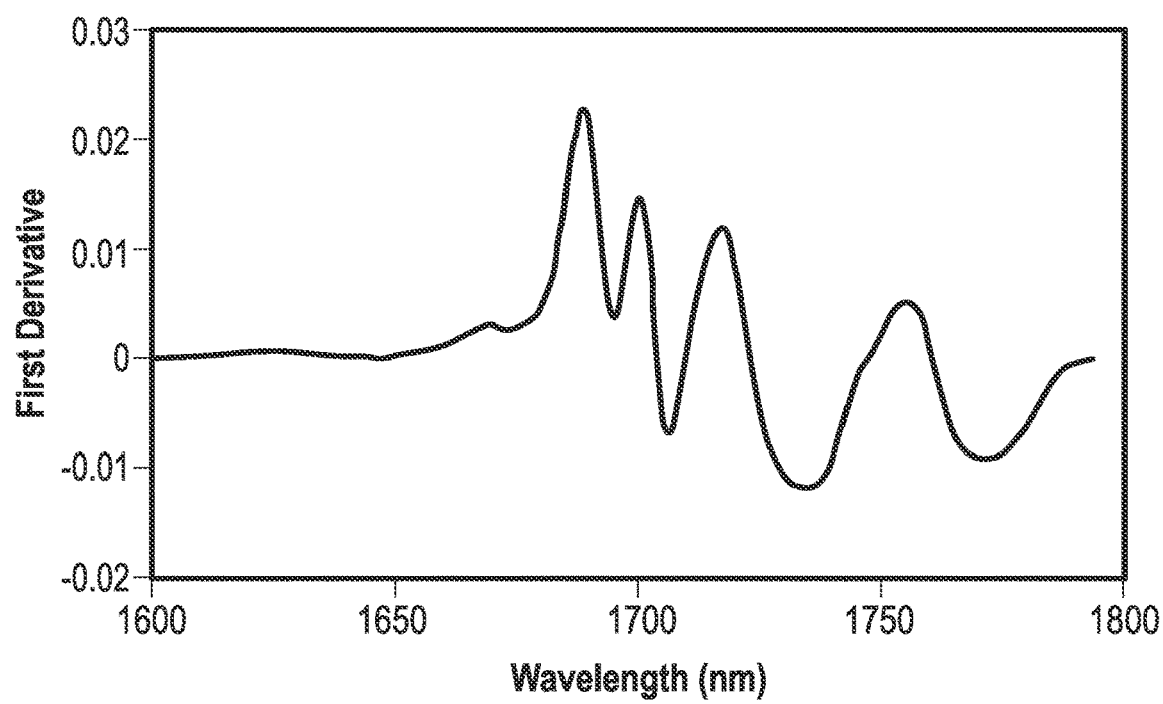
FIG. 12 is the first derivative of the absorption spectrum in the wavelength range between 1600 nm and 1800 nm.

In one embodiment, the vapor pressure value predicted by the NIR analyzer is monitored to control the process of the stabilizer in real time. FIG. 11 shows an NIR absorption spectrum of mid-stream production oil after a stabilizer, with the hydrocarbon absorption region between 1600 nm and 1800 nm, and FIG. 12 shows the first derivative of the absorption spectrum in the wavelength range between 1600 nm and 1800 nm. The light passes through the liquid fluid in the optical cell for at least one time before reaching a photodiode. The photo signal is converted to an absorption spectrum that is determined by the chemical composition of the fluid. During the calibration process, random samples are taken while the corresponding spectra are captured.

Figure 13:
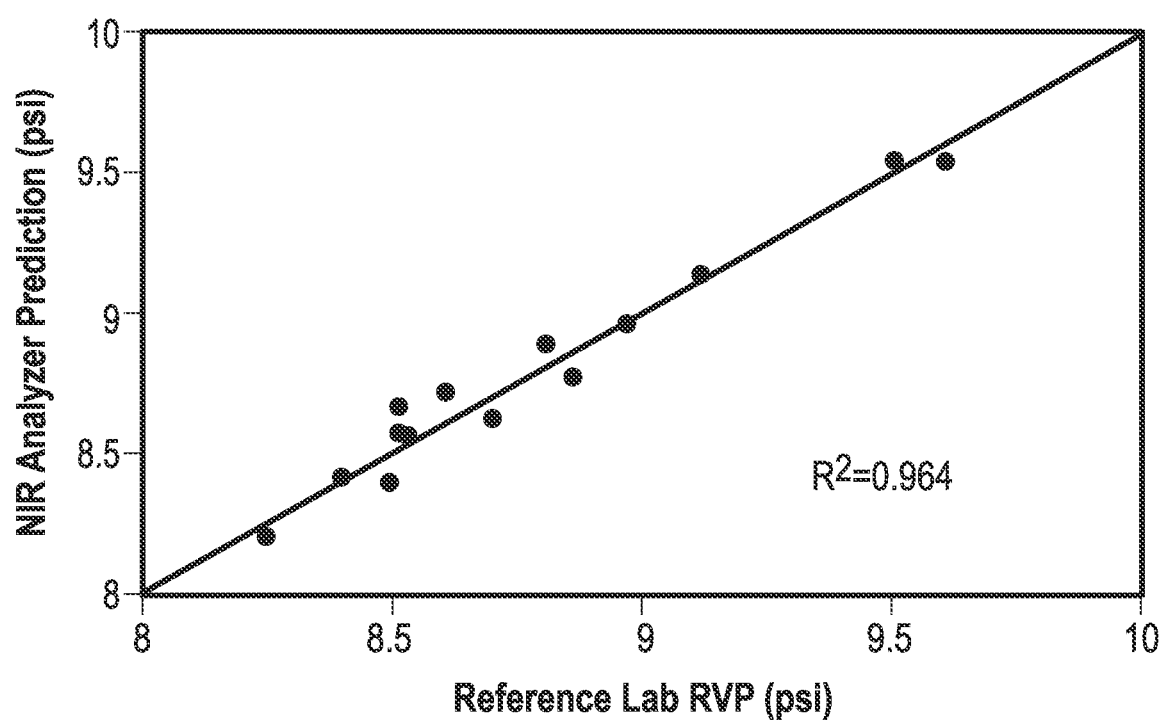
FIG. 13 is a chart in which the x-axis is the lab results of captured samples and y-axis is the NIR analyzer prediction.

FIG. 13 is a chart comparing the lab results in psi to the results determined by the chemometric modeling of the present invention.

In summary the present disclosure provides a chemical composition analyzer that may be used to optically determine and report chemical compositions associated with fluids within a fluid infrastructure. Once the composition is known, properties of interest, such as RVP, can be calculated for the fluid. This analyzer includes a number of remote optical sensors which may be used to perform spectroscopic spectrographic analysis in order to determine the chemical composition of the fluid. These sensors are tied to a data collection system to determine in a nearly continuous fashion the chemical composition associated with the fluid at various locations within the fluid infrastructure and thereby used to determine the RVP.

While the present system and method has been disclosed according to the preferred embodiment of the invention, those of ordinary skill in the art will understand that other embodiments have also been enabled. Even though the foregoing discussion has focused on particular embodiments, it is understood that other configurations are contemplated. In particular, even though the expressions "in one embodiment" or "in another embodiment" are used herein, these phrases are meant to generally reference embodiment possibilities and are not intended to limit the invention to those particular embodiment configurations. These terms may reference the same or different embodiments, and unless indicated otherwise, are combinable into aggregate embodiments. The terms "a", "an" and "the" mean "one or more" unless expressly specified otherwise. The term "connected" means "communicatively connected" unless otherwise defined.

When a single embodiment is described herein, it will be readily apparent that more than one embodiment may be used in place of a single embodiment. Similarly, where more than one embodiment is described herein, it will be readily apparent that a single embodiment may be substituted for that one device.

In light of the wide variety of methods for determining the composition of a fluid known in the art, the detailed embodiments are intended to be illustrative only and should not be taken as limiting the scope of the invention. Rather, what is claimed as the invention is all such modifications as may come within the spirit and scope of the following claims and equivalents thereto.

None of the description in this specification should be read as implying that any particular element, step or function is an essential element which must be included in the claim scope. The scope of the patented subject matter is defined only by the allowed claims and their equivalents. Unless explicitly recited, other aspects of the present invention as described in this specification do not limit the scope of the claims.

To aid the Patent Office and any readers of any patent issued on this application in interpreting the claims appended hereto, the applicant wishes to note that it does not intend any of the appended claims or claim elements to invoke 35 U.S.C. 112(f) unless the words "means for" or "step for" are explicitly used in the particular claim.

What is claimed is:

1. A system for determining vapor pressure of a liquid within a fluid infrastructure, comprising:
   a processing module;
   a sensor in fluid communication with an interior of the fluid infrastructure, and communicably connected with the processing module, the sensor configured to measure a composition of the liquid while in-situ and in real time; and
   a memory communicably connected with the processing module, and comprising a calibration model derived from measured compositions and measured vapor pressures of a plurality of samples of the liquid;
   wherein the processing module is configured to determine the composition of the liquid from a signal received from the sensor, to perform a correlation between a determined composition and the calibration model, and to return a vapor pressure based on the correlation.

2. The system for determining vapor pressure of a liquid of claim 1, wherein the calibration model comprises a calibration curve for predicting vapor pressure based on the composition of the liquid.

3. The system for determining vapor pressure of a liquid of claim 1, wherein the processing module is further configured to return the composition of the liquid in real time.

4. The system for determining vapor pressure of a liquid of claim 1, further comprising
- a control mechanism communicably connected to the processing unit and configured to control an operating condition upstream of the sensor;
- wherein the processing unit is configured to send a signal to the control mechanism responsive to a determination that the vapor pressure falls outside of a predetermined range; and
- wherein the control mechanism is configured to modify the operating condition responsive to its receipt of the signal.

5. The system for determining vapor pressure of a liquid of claim 4, wherein the control mechanism is configured to control addition of a stabilizer to the interior of the fluid infrastructure, and wherein the condition comprises a rate of addition of the stabilizer.

6. The system for determining vapor pressure of a liquid of claim 4, wherein the control mechanism is configured to control filtering equipment, and the operating condition comprises a filtering of the liquid.

7. The system for determining vapor pressure of a liquid of claim 1, wherein the sensor comprises a NIR analyzer.

8. The system for determining vapor pressure of a liquid of claim 7, wherein the NIR analyzer comprises a swept source laser.

9. The system for determining vapor pressure of a liquid of claim 7, wherein the NIR analyzer comprises a near infrared tunable laser.

10. The system for determining vapor pressure of a liquid of claim 1, wherein the correlation comprises using preprocessing to mitigate interferences.

11. The system for determining vapor pressure of a liquid of claim 7, wherein an output of a laser component of the NIR analyzer is monitored and fed back into the NIR analyzer, and wherein the laser component is configured to modify a characteristic of the output responsive thereto.

12. The system for determining vapor pressure of a liquid of claim 7, wherein the NIR analyzer scans across a wavelength range from about 1350 nm to about 1800 nm.

13. The system for determining vapor pressure of a liquid of claim 1, wherein the liquid is a condensate.

14. The system for determining vapor pressure of a liquid of claim 1, further comprising:
- a pressure sensor and a temperature sensor, each functionally connected to the interior of the fluid infrastructure and communicably connected to the processing module, the pressure sensor configured to determine a pressure in the fluid infrastructure in real time, the temperature sensor configured to determine a temperature of the liquid in real time; and
- wherein the processing module is further configured to receive the pressure from the pressure sensor and the temperature from the temperature sensor to use at least one of the pressure and the temperature in the correlation.

\* \* \* \* \*